United States Patent [19]

Cotting et al.

[11] Patent Number: 5,457,168

[45] Date of Patent: Oct. 10, 1995

[54] SOLID COMPOSITIONS OF POLYGLYCIDYL COMPOUNDS HAVING A MOLECULAR WEIGHT OF LESS THAN 1500

[75] Inventors: Jacques-Alain Cotting, Bonnefontaine, Switzerland; Philippe-Guilhaume Gottis, Mulhouse, France

[73] Assignee: Ciba-Geigy Corporation, Ardsley, N.Y.

[21] Appl. No.: 384,793

[22] Filed: Feb. 13, 1995

Related U.S. Application Data

[60] Continuation of Ser. No. 169,942, Feb. 2, 1994, abandoned, which is a division of Ser. No. 952,123, Sep. 28, 1992, Pat. No. 5,294,683.

[30] Foreign Application Priority Data

Oct. 3, 1991 [CH] Switzerland ............................ 2921/91

[51] Int. Cl.⁶ .................................................... C08L 63/00
[52] U.S. Cl. .......................... 525/533; 525/438; 525/524; 525/525; 525/531; 525/913; 525/934; 528/103; 528/103.5; 528/112
[58] Field of Search .................................. 525/438, 524, 525/525, 533, 531, 913, 934; 528/103, 103.5, 112

[56] References Cited

U.S. PATENT DOCUMENTS

| | | | |
|---|---|---|---|
| 3,095,429 | 6/1963 | Smith et al. | 549/541 |
| 3,344,117 | 9/1967 | Bamford et al. | 260/47 |
| 3,413,320 | 11/1968 | Cofer | 549/541 |
| 3,859,314 | 1/1975 | Dukes et al. | 260/348.6 |
| 4,102,701 | 7/1978 | Campbell et al. | 106/111 |

FOREIGN PATENT DOCUMENTS

| | | |
|---|---|---|
| 0006535 | 1/1980 | European Pat. Off. |
| 0018950 | 11/1980 | European Pat. Off. |
| 0178705 | 4/1986 | European Pat. Off. |
| 0383601 | 8/1990 | European Pat. Off. |
| 0462053 | 12/1991 | European Pat. Off. |
| 1158435 | 11/1963 | Germany. |
| 1643777 | 6/1973 | Germany. |
| 2319815 | 11/1973 | Germany. |
| 2609659 | 9/1976 | Germany. |
| 2602221 | 7/1977 | Germany. |
| 2602157 | 10/1984 | Germany. |
| 1033697 | 6/1966 | United Kingdom. |
| 1073633 | 6/1967 | United Kingdom. |
| 1186590 | 4/1970 | United Kingdom. |
| 1409835 | 10/1975 | United Kingdom. |
| 1516452 | 7/1978 | United Kingdom. |

OTHER PUBLICATIONS

Derwent Abstract 85–135281, Jun. 1983.
Org. Coat. Plas. Chem., 1979, 40, pp. 899–902 Kukiuchi et al.
Handbook of Epoxy Resins, Henry Lee, Kris Neville, MacGraw–Hill Inc., 1967, Appendix 5–1.
WPI Acc. No. 92–325881/40.
WPI Acc. No. 91–37101/51.

*Primary Examiner*—Melvyn I. Marquis
*Assistant Examiner*—Randy Gulakowski
*Attorney, Agent, or Firm*—William A. Teoli, Jr.

[57] ABSTRACT

There is disclosed a solid composition of polyglycidyl compounds having a molecular weight of less than 1500, which composition consists of one or more than one solid polyglycidyl compound and altogether not less than 5% by weight of one or of a mixture of more than one polyglycidyl compound, which compound or mixture is normally in liquid form, said amount being based on the total amount of all polyglycidyl compounds in the composition, which composition contains the said solid polyglycidyl compounds or at least part of the said solid polyglycidyl compounds in form of one or a mixture of more than one solid mixed phase, which solid mixed phase or mixture of more than one solid mixed phase essentially comprises the total amount of the polyglycidyl compounds which are normally in liquid form as additional component or components. Preferably the compositions are solid solutions of a solid polyglycidyl compound, typically diglycidyl terephthalate, and a further polyglycidyl compound which is normally in liquid form, for example triglycidyl trimellitate or triglycidyl trimesate. The compositions are suitable hardeners for powder coating compositions based on carboxyl-terminated polyesters.

3 Claims, No Drawings

SOLID COMPOSITIONS OF POLYGLYCIDYL COMPOUNDS HAVING A MOLECULAR WEIGHT OF LESS THAN 1500

This application is a continuation, of application Ser. No. 08/169,942, filed Feb. 2, 1994, now abandoned, which is a divisional of Ser. No. 07/952,123 filed Sep. 28, 1992, now U.S. Pat. No. 5,294,683.

The present invention relates to solid compositions of polyglycidyl compounds having a molecular weight of less than 1500 as main component, to a process for the preparation of said compositions, to the use thereof, and to a powder coating composition containing them.

Polyglycidyl compounds are often used at the present time as reactive components of curable compositions, typically as hardeners or curing agents in powder coating compositions based on polyesters. Many polyglycidyl compounds have the drawback that, in the form in which they are obtained, they are either liquid at ambient temperature or at moderately elevated temperature, or they can only be obtained with a justifiable expenditure of time and effort in a form in which they are liquid or semi-solid at the stated temperatures because of impurities. To blend these liquid compounds homogeneously into solid formulations requires in practice technically very much more complicated procedures than are necessary if only solid glycidyl compounds are used.

However, diglycidyl compounds constitute the main component of the known solid polyglycidyl compounds. These compounds have in turn other disadvantages if used as single curing agent for curable compositions. For example, diglycidyl compounds are in general less reactive than higher functional polyglycidyl compounds and effect a lower degree of crosslinking. Their utilities are correspondingly limited.

Although some few higher functional polyglycidyl compounds, including triglycidyl trimesate or, in particular, triglycidyl isocyanurate, may also be obtained in solid form, it requires either unusual and costly procedures or rather complicated and hence also expensive purification operations to do so. Nevertheless, solid triglycidyl isocyanurate has achieved a unique status in many fields of use for glycidyl hardeners, although some liquid or semi-solid glycidyl compounds have become known which match or even surpass it as curing agent with respect to the properties of the finished formulations or the cured products obtained therefrom. Liquid polydiglycidyl compounds of this type are disclosed in EP-A-0 506 617 and in EP-A-0 383 601 (published on 22 Aug. 1990).

In order that polyglycidyl compounds in liquid form may also be used in simple manner as hardeners for solid compositions, the proposal has already been made in the prior art to solidify said compounds by blending them with specific other substances. For example, EP-A-0 178 705 (published on 23 Apr. 1986) discloses a solid composition which consists of highly impure, and hence liquid, triglycidyl isocyanurate and a non-reactive, readily crystallisable polyester, and which is a suitable hardener for carboxyl-terminated polyesters. EP-A-0 462 053 discloses a solid composition comprising liquid or semi-solid glycidyl compounds and a solid condensation polymer of large pore size, which composition is prepared from urea or melamine and formaldehyde. The drawback of these compositions is that they contain fairly large amounts of inch substances, i.e. substances which do not themselves effect hardening. The consequence is that these hardeners have an unnecessarily low epoxy content, thereby necessitating the use of rather large amounts of hardener, which in turn results, inter alia, in higher costs.

It is the object of this invention to provide novel solid compositions based on polylycidyl compounds which are normally in liquid form, which compositions substantially contain no inert components.

Surprisingly, it has been found that low molecular solid polyglycidyl compounds are often able to absorb or dissolve large amounts of other polyglycidyl compounds of similar molecular weight which are normally in liquid form to form non-tacky solid compositions.

Accordingly, the invention relates to a a solid composition of polyglycidyl compounds having a molecular weight of less than 1500, which composition consists of one or more than one solid polyglycidyl compound and altogether not less than 5% by weight of one or of a mixture of more than one polyglycidyl compound, which compound or mixture is normally in liquid form, said amount being based on the total amount of all polyglycidyl compounds in the composition, which composition contains the said solid polyglycidyl compounds or at least part of the said solid polyglycidyl compounds in form of one or a mixture of more than one solid mixed phase, which solid mixed phase or mixture of more than one solid mixed phase essentially comprises the total amount of the polyglycidyl compounds which are normally in liquid form as additional component or components.

The novel compositions are virtually non-tacky.

The novel compositions are preferably solid mixed phases (solid solutions) of a solid polyglycidyl compound and a further polyglycidyl compound which is normally in liquid form. The presence of a a solid solution can conveniently be determined by means of X-ray diffractometry, as the positions of the reflexes in the X-ray diffractogram of such a composition usually differ only immaterially from those in the diffractogram of the pure solid polyglycidyl compound.

The term "polyglycidyl compounds" embraces in this context compounds which carry unsubstituted glycidyl groups, and also compounds which carry e.g. methyl-substituted glycidyl groups. The polyglycidyl compounds in the novel composition preferably have a molecular weight in the range from 200 to 1200, more particularly from 200 to 1000. They should have an epoxy value which is normally greater than 3.5 epoxide equivalents per kilogram of the compound, preferably at least 4 equivalents, most preferably 5 and more equivalents per kilogram.

Suitable polyglycidyl compounds are those having melting points higher than ambient temperature (c. 25° C.) to c. 250° C. Preferably, however, the melting points of the compounds are in the range from 60° to 150° C. It will be readily appreciated that the melting points need not be quite sharp as they are generally known to be in the case of contaminated compounds.

The expression "polyglycidyl compounds which are normally in liquid form" will be understood as meaning polyglycidyl compounds which, at ambient temperature, i.e. at c. 15°–25° C., or at only slightly elevated temperature, typically at 30° or 40° C., are in an already perceptibly fluid form. This expression embraces pure polyglycidyl compounds whose melting point is below the stated temperatures, and also those forms of polyglycidyl compounds which, in high purity, would be solid at the stated temperatures, but none the less in the actual starting form in which they are used for the preparation of the novel compositions are liquid. Such forms may typically be technical crude forms of specific polyglycidyl compounds. For example, triglycidyl isocyanurate, which in the course of its synthesis is often initially obtained as an oil, can be used in this form as liquid polyglycidyl component for the novel compositions. The same applies also to triglycidyl trimesate which, although starting from the expensive and only sparingly available glycidol as one component, is fairly readily obtainable in solid form, but is only obtainable in an impure form which is liquid at ambient temperature in the standard reaction of the appropriate acid with epichlorohydrin for the industrial production of glycidyl esters.

The polyglycidyl compounds which are normally in liquid form generally and preferably have a higher functionality than the solid polyglycidyl compounds and typically contain at least three glycidyl groups per molecule. They preferably have an epoxy value of 5.5 and more epoxide equivalents per kilogram of the compound.

Preferably the novel compositions consist of polyglycidyl compounds which carry glycidyl ether and/or glycidyl ester groups. A polyglycidyl compound can also carry both kinds of glycidyl groups, typically glycidyl 4-glycidyloxybenzoate which may be used in the practice of this invention as solid polyglycidyl compound.

Other especially preferred solid polyglycidyl compounds are diglycidyl esters and/or diglycidyl ethers.

The diglycidyl esters may be derived from aromatic, araliphatic, cycloaliphatic, heterocyclic, heterocyclic-aliphatic and heterocyclic-aromatic dicarboxylic acids containing 6 to 20, preferably 6 to 12, ring carbon atoms, or from aliphatic dicarboxylic acids containing 2 to 10 carbon atoms. Compounds of this type are commonly known and described, inter alia, in U.S. Pat. No. 3,859,314 or in DE-A-31 26 411 (published on 13 Jan. 1983). Typical examples of suitable dicarboxylic acids are: phthalic acid, isophthalic acid, terephthalic acid, 2,5-dimethylphthalic acid, naphthalene-2,6-dicarboxylic acid, naphthalene-1,8-dicarboxylic acid, naphthalene-2,3-dicarboxylic acid, diphenyl ether 4,4'-dicarboxylic acid, diphenyl-2,2'-dicarboxylic acid, tetrachlorophthalic acid, 2,5-dichlorophthalic acid, o-, m- or p-phenylenediacetic acid, oxalic acid, malonic acid, succinic acid, adipic acid, 2,2,4-trimethyladipic acid, 2,4,4-trimethyladipic acid, sebacic acid, azelaic acid, fumaric acid, maleic acid and the dicarboxylic acids obtainable by addition of acrylonitrile or acrylate to compounds having activatable hydrogen atoms, typically ketones, nitrogen compounds, diols or dithiols, tetrahydrophthalic acid, methyltetrahydrophthalic acid, hexahydrophthalic acid, methylhexahydrophthalic acid, endomethylenehexahydrophthalic acid, hexahydroterephthalic acid, hexahydroisophthalic acid, thiophene-2,5-dicarboxylic acid, furan-2,5-dicarboxylic acid, furan-3,4-dicarboxylic acid, pyrazine-3,4-dicarboxylic acid, unsubstituted 1,3-bis(carboxyethyl)hydantoin or 1,3-bis(carboxyethyl)hydantoin which is alkyl-substituted in 5-position, 1,1-methylenebis[3-(p-glycidyloxycarbonylbenzyl)-5,5-dimethylhydantoin], as well as other dicarboxylic acids which contain one or more hydantoin rings, and N,N'-bis(p-glycidyloxycarbonylbenzoyl)isophoronediamine.

Particularly preferred compositions are those in which the diglycidyl esters are diglycidyl terephthalate or diglycidyl isophthalate, or diglycidyl trans-hexahydrophthalate, or diglycidyl oxalate or diglycidyl adipate or diglycidyl sebacate, or diglycidyl azelate or diglycidyl succinate.

Suitable solid polyglycidyl ethers include compounds carrying glycidylised aromatic hydroxyl groups, preferably the diglycidyl ethers which are derived from

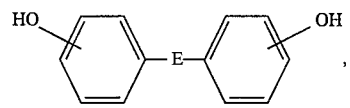

preferably from

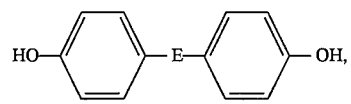

wherein E in each formula is —CH$_2$—, —C(CH$_3$)$_2$—, —O—, —S—, —SO— or, preferably, —SO$_2$—.

A further special embodiment of the novel compositions contains as solid polyglycidyl compound a diglycidyl ether of formula (I):

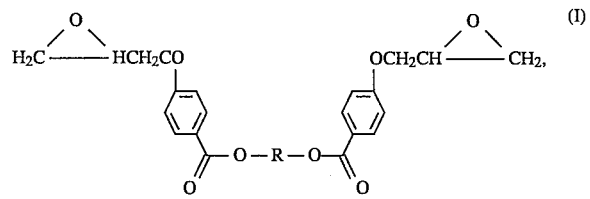

wherein R is an organic divalent radical of 2 to 15 carbon atoms.

The divalent radicals R are preferably those derived from diols R(OH)$_2$ which are also customarily used as starting materials for polyesters, typically 1,2-ethanediyl, 1,2-propanediyl, 1,3-butanediyl and 1,4-butanediyl, 2,2-dimethyl-1,3-propanediyl, 1,6-hexanediyl, 2-ethyl-1,3-hexanediyl or groups of formula:

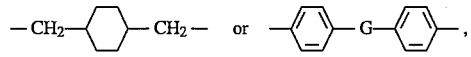

or
wherein G is —CH$_2$—, —C(CH$_3$)$_2$—, —O—, —S—, —SO— or —SO$_2$—.

Particularly preferred radicals R are 1,3-butanediyl, 1,6-hexanediyl,

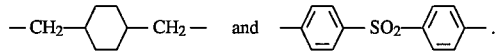

The cited compounds, some of which are novel, can be obtained by conventional methods, typically by transesterifying methyl 4-hydroxybenzoate with the appropriate diol R(OH)$_2$ and then glycidylising with epichlorohydrin. Another similar process is described by H. KAKIUCHI und S. TAKEI in "New Epoxy Resins from Alkylene-bis-(p-hydroxy benzoate)", Org. Coat. Plast. Chem. 1979, 40, 899–902.

The polyglycidyl compounds which are normally in liquid form embrace in particular polyglycidyl ethers and esters carrying three or more glycidyl groups per molecule, such as polyglycidyl esters of benzenepolycarboxylic acids, typically 1,2,3-benzenetricarboxylic acid (hemimellitic acid), 1,2,4-benzenetricarboxylic acid (trimellitic acid), 1,3,5-benzenetricarboxylic acid (trimesic acid), 1,2,3,4-benzenetetracarboxylic acid (mellophanic acid), 1,2,3,5-benzenetetracarboxylic acid, benzenepentacarboxylic acid and benzenehexacarboxylic acid (mellitic acid), naphthalenetetracarboxylic acid, perylenetetracarboxylic acid, or tetracarboxylic acids of formula

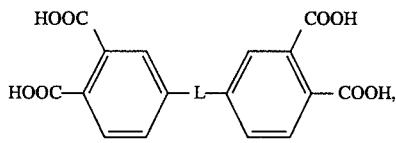

wherein L is —CH$_2$—, —C(CH$_3$)$_2$—, —O—, —S—, —SO— or —SO$_2$ , preferably benzophenone-3,3',4,4'-tetracarboxylic acid. Such polyglycidyl esters can be prepared by known methods, conveniently by the methods described in the publications cited in connection with the diglycidyl esters.

Particularly preferred compositions are those which contain polyglycidyl esters carrying at least three glycidyl groups per molecule as polyglycidyl compounds which are normally in liquid form, typically polyglycidyl esters carrying three or four glycidyl groups, preferably selected from non-solid forms of triglycidyl trimellitate, triglycidyl trimesate and tetraglycidyl pyromellitate.

Suitable glycidyl esters in the novel composition are also the compounds of formulae (II) or (III):

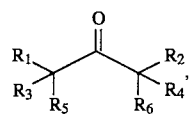

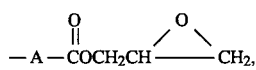

wherein R$_1$, R$_2$, R$_3$ and R$_4$ in formula (II) are each independently of one another hydrogen, C$_1$–C$_4$alkyl or radicals of formula (IV):

$$-A-\overset{O}{\overset{\|}{C}}OCH_2CH\overset{O}{\diagup}\diagdown CH_2,\quad(IV)$$

wherein A is a polymethylene group of 2 to 4 carbon atoms, and R$_5$ and R$_6$ are each independently of the other hydrogen, C$_1$–C$_4$alkyl, radicals of formula (IV) or, taken together, are an unsubstituted or a C$_1$–C$_4$alkyl-substituted methylene or polymethylene group of 2 to 7 carbon atoms, and, in formula (III), n is an integer from 2 to 6, R$_7$ is an organic radical of valency n, and the substituents Z are identical or different radicals of formula (V):

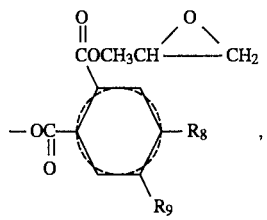

wherein R$_8$ and R$_9$ are either each independently of the other hydrogen, chloro, bromo or C$_1$–C$_4$alkyl, or one of R$_8$ and R$_9$ is a radical of formula (VI):

$$-\overset{O}{\overset{\|}{C}}OCH_2CH\overset{O}{\diagup}\diagdown CH_2,\quad(VI)$$

and the other is hydrogen, chloro, bromo or C$_1$–C$_4$alkyl, and the six-membered ring in formula (V) is aromatic or non-aromatic.

The number of glycidyl groups per molecule in the cited compounds is in this case too not fewer than three.

In formula (II), R$_1$ to R$_4$ are preferably a radical of formula (IV) and R$_5$ and R$_6$ together are preferably an unsubstituted or a C$_1$–C$_4$alkyl-substituted methylene or polymethylene group of 2 to 7 carbon atoms, preferably an unsubstituted polymethylene group of 2 to 4 carbon atoms. Although the number of alkyl substituents may be up to twice the number of carbon atoms of the methylene or polymethylene group, it should desirably be 1 or or 2. In formula (IV), A is preferably an ethylene group. Exemplary of suitable compounds of formula (II) are the tetraglycidyl ester of 2,2,5,5-tetra(β-carboxyethyl)cyclopentanone, the tetraglycidyl ester of 2,2,6,6-tetra(β-carboxyethyl)cyclohexanone, and the tetraglycidyl ester of 2,2,4,4-tetra(β-carboxyethyl)pentan-3-one or the tetraglycidyl ester of 1,1,3,3-tetra(β-carboxyethyl)acetone.

The compounds of formula (II) are obtainable from the corresponding polycarboxylic acids, conveniently by reacting the carboxylic acids with epihalohydrin to give the halohydrin esters, halogen being preferably bromo and, more particularly, chloro. The halohydrin esters can subsequently be dehydrohalogenated with hydrogen halide acceptors to the corresponding glycidyl esters, as described in more detail, inter alia, in DE-A-23 19 815 (=GB 1 409 835), published on 22 Nov. 1973. The starting cycloaliphatic polycarboxylic acids can be prepared in accordance with GB patent specification 1 033 697 (=U.S. Pat. No. 3,344,117), published on 22 Jun. 1966, and the aliphatic polycarboxylic acids can be prepared in general accordance with DE-A-26 09 659 (=U.S. Pat. No. 4,102,701), published on 30 Sep. 1976.

In formula (III) R$_7$ is preferably a divalent to hexavalent, more particularly a divalent, trivalent or tetravalent, aliphatic radical of 2 to 10 carbon atoms, a corresponding cycloaliphatic or aromatic radical containing 5 to 10 ring carbon atoms or an araliphatic radical containing 5 to 20 ring carbon atoms. These radicals may also contain hetero atoms. The radicals R$_7$ can be considered as the residues of polyalcohols or polyols from which the hydroxyl groups have been removed in an amount corresponding to one of the valences given above. Particularly preferred radicals R$_7$ are those derived from straight chain and branched chain aliphatic polyols, typically from glycols such as ethylene or propylene glycol, from glycerol, trimethylolpropane, erythritol or pentaerythritol. Preferred polyols are also bisphenol types, typically 2,2-bis(4-hydroxyphenyl)propane or bis(4-hydroxyphenyl)methane, and similar wholly or partially saturated saturated compounds, for example 2,2-bis(4-hydroxycyclohexyl)propane. Another example is sorbitol. In some cases the polyols can also be dimeriser or prepolymerised, i.e. they can be polyether alcohols such as polyethylene glycols or bis(trimethylol)propane. The prepolymers preferably have a degree of polymerisation of 2 to 6. The six-membered carbon ring in formula (V) can be either aromatic or cycloaliphatic, in which latter case it may be wholly or only partially saturated. It may carry further substituents, typically chloro, bromo or C$_1$–C$_4$alkyl. Depending on the degree of saturation of the ring, the ring may carry up to 10 substituents; but for practical reasons it will expediently carry not more than 4 substituents. Most preferably, however, the ting will contain only the glycidyl ester groups as substituents. The individual substituents Z in formula (III) may also be different. They also need not have the identical number of glycidyl ester groups.

The compounds of formula (III) can be obtained in the following manner. First the chosen polyalcohol is reacted to the hemiester with phthalic, tetrahydrophthalic, hexahydrophthalic or trimellitic anhydride in the appropriate stoichiometric ratio. In the case of trimelletic anhydride, which carries a carboxyl group in addition to the anhydride group, virtually only the anhydride group reacts to a hemiester still carrying two free carboxyl groups. The carboxyl groups can subsequently be glycidylised with epihalohydrin, preferably epichlorohydrin, as described above in respect of the compounds of formula (II).

If compounds of formulae (II) and (III) are solid, as in particular many compounds of formula (III) carrying two glycidyl ester groups are, for example the glycidylised hemiester of hydrogenated bisphenol A and phthalic acid, the compounds may of course also be used as solid polyglycidyl compounds in the novel compositions.

Further suitable liquid polyglycidyl compounds are tri- or tetraglycidyl ethers of formula VII:

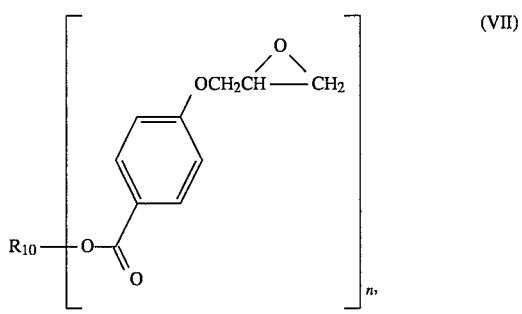

(VII)

wherein n may be 3 or 4 and $R_{10}$ is an organic trivalent or tetravalent radical of 2 to 15 carbon atoms.

The radical $R_{10}$ is preferably a radical derived from triols or tetraols which are likewise commonly used as starting materials for obtaining polyesters, and preferably denotes groups of formulae:

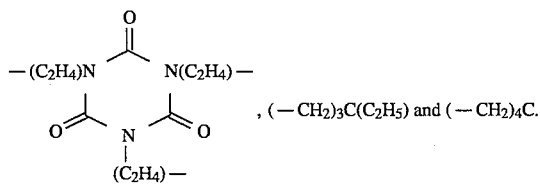

, $(-CH_2)_3C(C_2H_5)$ and $(-CH_2)_4C$.

The compounds are obtainable in the same manner as described above in connection with the corresponding diglycidyl ethers and some are also novel.

Although the polyglycidyl compounds in solid form and those normally in liquid form of which the novel compositions consist are usually compounds of differing chemical formula, this does not necessarily have to so. Novel compositions are also obtainable from a specific solid polyglycidyl compound and a proportion of a substance the main component of which does have the same chemical formula as the solid glycidyl compound, but which is fluid at ambient temperature on account of impurities. A composition obtained by applying the special principle of the invention will consist typically of solid triglycidyl trimesate which has been obtained by reacting trimesic acid or an ester thereof and glycidol (e.g. in accordance with DE-C-26 02 157), and of triglycidyl trimesate which may be obtained from trimesic acid and epichlorohydrin (e.g. in accordance with DE-B-16 43 777), and which is in a form that is liquid at ambient temperature.

The maximum concentration that the novel compositions may have of polyglycidyl compounds which are normally in liquid form can vary over a wide range, depending on the solid and liquid polyglycidyl components and their solubility in one another, and may readily be determined by the person skilled in the an with the aid of one or two experiments. Very often this maximum concentration is at least 45 percent by weight. In a preferred embodiment of the invention, the novel compositions therefore contain a total amount of 5 to 45 percent by weight of polyglycidyl compounds which are normally in liquid form, which amount is based on the total amount of all polyglycidyl compounds present in the composition. The most preferred concentration range of liquid polyglycidyl compounds present in the compositions is from 15 to 35 percent by weight.

Preferably the novel compositions have an epoxy value of more than 4.5 equivalents per kilogram of the composition. Compositions having an epoxy value of 6 and more equivalents are especially preferred.

The novel compositions are solid and non-tacky at least at ambient temperature (20°–25° C.) and at low temperature. Their softening range is preferably from 40° to 250° C., more particularly from 60° to 120° C.

In a special embodiment of the novel compositions, the solid polyglycidyl compounds are bifunctional and the polyglycidyl compounds which are normally in liquid form are at least trifunctional. Compositions of this type have hardening properties which are essentially similar to those of triglycidyl isocyanurate. This feature is of particular importance because the special status of triglycidyl isocyanurate among the polyglycidyl compounds mentioned at the outset has resulted in reactants for glycidyl hardeners being optimised for the use of triglycidyl isocyanurate in particular as curing agent, so that at present virtually only such components are commercially available for many fields of use. As a consequence of this optimisation, these components in general exhibit only poor properties when used alone with diglycidyl compounds as hardeners.

Especially preferred compositions of the last mentioned kind are those which constitute a solid solution of 60 to 85, preferably 75 to 85, percent by weight of diglycidyl terephthalate and a total amount of 15 to 40, preferably 15 to 25 percent by weight of triglycidyl trimellitic acid and/or liquid triglycidyl trimesate, typically a composition comprising 75 percent by weight of diglycidyl terephthalate and 25 percent by weight of triglycidyl trimellitate.

The above described solid compositions of polyglycidyl compounds as essential component are generally obtainable by a process in the course of which one or more than one solid polyglycidyl compound, together with altogether not less than 5 percent by weight, based on the total amount of polyglycidyl compounds, of one or of a mixture of more than one polyglycidyl compound, which compound or mixture is in liquid form at ambient temperature, are heated until said polyglycidyl compounds form a substantially homogeneous liquid mixture, and the temperature is lowered in the further course of the process at least sufficiently for the solid product to form.

A solid product obtained by the above described process is, finally, preferably granulated. The powder particles obtained after granulation do not agglomerate and stick together at normal storage temperatures (ambient or moderately elevated temperature), and are also in other respects physically and chemically stable.

It is, however, also possible to dissolve the solid and liquid polyglycidyl compounds intended for the composition in a suitable solvent and to remove all solvent from the combined solutions sufficiently that the novel solid compositions can be obtained.

In the same manner it is also possible to glycidylise specific compounds jointly, typically polycarboxylic acids and/or polycarboxylic anhydrides, which form polyglycidyl esters which are normally in liquid form, in admixture with a sufficient amount of polycarboxylic acids and/or polycarboxylic anhydrides which form solid glycidyl esters. This particularly simple manner of preparing novel compositions which consist of polyglycidyl esters, is especially preferred. The invention accordingly also relates to a process for the preparation of a composition as described above and consisting of polyglycidyl esters as polyglycidyl compounds, which process comprises converting one or more than one compound selected from polycarboxylic acids and polycarboxylic anhydrides which form solid polyglycidyl esters, in admixture with one or more than one compound selected from polycarboxylic acids and polycarboxylic anhydrides which form polyglycidyl esters that are normally in liquid form, into glycidyl esters, the amounts of polycarboxylic acids being so chosen that one or more than one solid mixed phase forms, which solid mixed phase or mixture of more than one solid mixed phase essentially comprises the total amount of the polyglycidyl compounds which are normally in liquid form as additional component or components.

The above process is well suited for preparing novel compositions on the basis of diglycidyl terephthalate, diglycidyl isophthalate, or diglycidyl trans-hexahydrophthalate, triglycidyl trimellitate, triglycidyl trimesate and tetraglycidyl pyromellitate.

The joint conversion of the mixture of polycarboxylic acids into the corresponding polyglycidyl esters can in principle be carried out by any suitable process therefor. One process is disclosed in DE-B-1 643 777 (German Auslegeschrift published on 14 Jun. 1973), reference to which is merely made here, but the disclosure of which is regarded as impart of this description. The process disclosed in DE-B-1 643 777 is preeminently suitable for the preparation of novel compositions based on 60 to 85 percent by weight of diglycidyl terephthalate and altogether 15 to 40 percent by weight of triglycidyl trimellitate and/or liquid forms of triglycidyl trimesate, e.g. of about 75 percent by weight of diglycidyl terephthalate and about 25 percent by weight of triglycidyl trimesate.

The novel compositions are particularly suitable, inter alia, as curing agents or hardeners for substances which carry functional groups which react with epoxy groups, typically hydroxyl, thiol, amino, amido or, preferably, carboxyl groups. Further examples of functional groups are described in Henry Lee, Kris Neville, "Handbook of Epoxy Resins", MacGraw-Hill, Inc. 1967, Appendix 5-1. For many functional groups the addition of a catalyst may be useful. Mixtures of this kind can generally be cured in the temperature range from 100° to 250° C. and have many utilities, typically as melt adhesives, casting resins or moulding compounds. The preferred utility is as curing agent for those epoxy group containing substances which are solid at ambient or moderately elevated temperature.

A particularly preferred field of use of the novel compositions is powder coating compositions. For this utility, the novel compositions are able to replace the generally more toxic triglycidyl isocyanurate which finds particularly wide application in this technology, usually without essential changes of the other components of the powder coating compositions or of the production of the finishes being necessary and without having to take into account disadvantages in respect of the technical aspects of their use.

The invention thus also relates to powder coating compositions, preferably based on polyesters containing free carboxyl groups, which contain one of the above described compositions and use them as curing agents.

These powder coating compositions are based on polyesters which carry terminal carboxyl groups and are normally used in this technology. Preferably the polyesters have an acid number (given in mg of KOH/g of polyester) of 10 to 100 and a molecular weight of 500 to 10 000, preferably of up to 2000. The polyesters are preferably solid at room temperature and have a glass transition temperature of 35° to 120° C., preferably of 40° to 80° C.

The polyesters described in the foregoing paragraph are disclosed in U.S. Pat. No. 3,397,254. They are reaction products of polyols with dicarboxylic acids and, in some cases, polyfunctional carboxylic acids. Representative examples of suitable polyols are ethylene glycol, propylene glycol, 1,3-butanediol, 1,4-butanediol, neopentanediol, isopentyl glycol, 1,6-hexanediol, glycerol, trimethylolethane, trimethylolpropane, erythritol, pentaerythritol or cyclohexanediol. In particular neopentanediol constitutes an essential constituent of the polyester resins which are suitable for very durable coatings. Typical examples of suitable dicarboxylic acids are isophthalic acid, terephthalic acid, phthalic acid, methylphthalic acids, tetrahydrophthalic acid, methyltetrahydrophthalic acids, for example 4-methyltetrahydrophthalic acid, cyclohexanedicarboxylic acid, succinic acid, glutaric acid, adipic acid, pimelic acid, suberic acid, azelaic acid, sebacic acid, fumaric acid, maleic acid, or 4,4'-diphenyldicarboxylic acid and the like. Suitable tricarboxylic anhydrides are the anhydrides of aliphatic tricarboxylic acid, such as 1,2,3-propanetricarboxylic acid, of aromatic tricarboxylic acid, such as trimellitic acid (benzene-1,2,4-tricarboxylic acid) and hemimellitic acid (benzene-1,2,3-tricarboxylic acid), or of cycloaliphatic tricarboxylic acid, such as 6-methylcyclohex-4-ene-1,2,3-tricarboxylic acid. Exemplary of suitable tetracarboxylic anhydrides are pyromellitic dianhydride or benzophenone-3,3',4,4'-tetracarboxylic dianhydride.

The novel compositions are preferably used in an amount such that the ratio of carboxyl groups to epoxy groups in the powder coating composition is from 0.5:1 to 2:1.

The powder coating compositions naturally contain still other modifiers conventionally used in the coating industry, typically light stabilisers, dyes, pigments such as titanium dioxide pigment, dearating agents such as benzoin, and/or flow control agents. Suitable flow control agents are typically polyvinyl acetals such as polyvinyl butyral, polyethylene glycol, polyvinyl pyrrolidone, glycerol, and the acrylic copolymers available under the registered trademarks Modaflow® [MONSANTO] or Acrylron® [PROTEX].

The powder coating compositions of this invention can be prepared by simple mixing of the components, conveniently in a ball mill. Another possibility comprises fusing, mixing and homogenising the components together, preferably in an extruder, as in a Buss Ko-kneader, cooling the product and comminuting it. The powder coating compositions preferably have a particle size in the range from 0.015 to 500 μm, most preferably from 10 to 75 μm.

After application to the coated object, the powder coating compositions are cured at a temperature of not less than c. 100° C., preferably 150° to 250° C. Normally about 5 to 60 minutes are required for the cure. Suitable for coating are all materials which are stable at the temperatures necessary for the cure, preferably ceramic materials and metals.

The use in particular of polyesters which contain more than 50 percent by weight, preferably up to 90 percent by weight and more, of neopentanediol and aromatic dicarboxylic acids, preferably terephthalic acid, as components, and which are commercially available as Crylcoat® types [UCB] or under registered trademarks such as Uralac® [DSM] or Grilesta® [EMS], results in powder coating compositions with which durable outdoor and particularly flexible finishes are obtained, as regards both sudden as well as permanent mechanical stress.

EXAMPLE 1

100 g of triglycidyl trimellitate [viscous product with an epoxy value of 6.91 epoxide equivalents/kg (theory: 7.92 epoxide equivalents/kg), prepared in accordance with DE-A-16 43 777, Example 15, published on 8 Jun. 1972] are mixed with 400 g of diglycidyl terephthalate [solid product having a melting range of 97°–103° C. and an epoxy value of 6.40 epoxide equivalents/kg (89% of theory), prepared in accordance with DE-A-16 43 777, Example 7]. The temperature of the mixture is raised to 105° C. until the solution is clear. The mixture is then cooled, whereupon a colourless, crystalline and non-tacky product with a melting point of 92° C. and an epoxy value of 6.75 epoxide equivalents/kg is obtained in quantitative yield.

EXAMPLE 2

125 g of the triglycidyl trimellitate used in Example 1 are mixed with 375 g of the diglycidyl terephthalate used in Example 1. The temperature of the mixture is raised to 105° C. until the solution is clear. The mixture is then cooled, whereupon a colourless, crystalline and non-tacky product with a melting point of 83° C. and an epoxy value of 6.83 epoxide equivalents/kg is obtained in quantitative yield.

EXAMPLE 3

100 g of the tetraglycidyl ester of 2,2,6,6-tetra(β-carboxyethyl)cyclohexanone (epoxy value of 5.29 lepoxide equivalents/kg, prepared in accordance with DE-A-23 19 815), are blended with 300 g of diglycidyl terephthalate [solid product having a melting range of 97°–103° C. and an epoxy value of 6.40 epoxide equivalents/kg (89% of theory), prepared in accordance with DE-A-16 43 777, Example 7]. The temperature of the mixture is raised to 105° C. until the solution is clear. The mixture is then cooled, whereupon a colourless, crystalline and non-tacky product with a melting point of 83° C. and an epoxy value of 6.32 epoxide equivalents/kg is obtained in quantitative yield.

EXAMPLE 4

Preparation and glycidylation of the bis(4-hydroxybenzoate) of 1,6-hexanediol 413.6 g (3.5 mol) of 1,6-hexanediol are fused at a temperature of c. 60° C. Then 1065.05 g (7 mol) of methyl 4-hydroxybenzoate and 2.95 g of tetrabutyl orthotitanate are added. The reaction mixture is thereafter heated under nitrogen for 4 hours to 210° C. Yield: 1254.7 g of the bis(4-hydroxybenzoate) of 1,6-hexanediol in the form of a solid product (softening point: 176° C.), corresponding to a bulk yield of 99.8% with a phenol content of 5.52 phenol equivalents/kg (=99% of theory).

1000 g of this product are reacted with 3574 g (38.6 mol) of epichlorohydrin while keeping the temperature at 90° C. Then 32.24 g of a 50% aqueous solution of tetramethylammonium chloride are added. The temperature is kept in the range from 85° to 90° C., and the reaction course is monitored with the aid of a pH electrode. After c. 150 minutes, the pH meter registers a sudden increase to a c. 9.4, thereby indicating the end of the addition reaction. After removal of the pH electrode, the reaction mixture is cooled to 50° C. Under a vacuum of 0.09 to 0.13 bar and at a temperature of 45°–50° C., 485.7 g of an aqueous solution of sodium hydroxide are run in continuously over 300 minutes, while distilling water from the reaction mixture with epichlorohydrin as an azeotropic mixture. The epichlorohydrin is separated from the water in a water separator and returned to the reaction mixture continuously. The reaction mixture is then washed with 400 ml of an aqueous 10% solution of monosodium phosphate and with 3×500 ml of water. Yield: 1089.4 g (84% of theory) of bis(4-glycidyloxybenzoate) of 1,6-hexanediol in the form of a solid product (melting point 120° C., epoxy value 4.24 epoxide equivalents/kg, corresponding to 100% of theory, chlorine content 0.15%).

EXAMPLE 5

260 g of the product of Example 4 are mixed with 140 g of triglycidyl trimellitate. The temperature of the mixture is raised to 130° C. until the solution becomes clear. The mixture is then cooled, wherepon a colourless, crystalline product with a melting point of 115° C. and an epoxy value of 5.12 epoxide equivalents/kg is obtained in quantitative yield.

EXAMPLE 6

A mixture of 930 g of Crylcoat® 430 [carboxyl-terminated polyester based on neopentanediol and terephthalic acid with an acid number of c. 30 mg KOH/g and a glass transition temperature ($T_G$) of c. 70° C. (DSC), ex UCB, Belgium], 97 g of the product of Example 1, 11 g of Acrylron® solid (flow control agent based on a butylated polyacrylate), 2 g of benzoin, 30 g of a curing catalyst based on a concentrate of a tetraalkylammonium bromide salt and 500 g of titanium dioxide, is homogenised in an extruder (Ko-kneader, supplied by Buss, Pratreln, CH). The cooled extrudate is comminuted to the finished powder coating composition having a particle size of c. 40 μm.

This composition is sprayed electrostatically onto an aluminium sheet. After stoving for 10 minutes at a temperature of 200° C. a film having the following properties is obtained:

| | |
|---|---|
| film thickness | 55 μm |
| impact strength | 160 kg · cm |
| Erichsen cupping test (DIN 53 156) | 10 mm |
| gloss at an angle of 60° | 90% |
| flow at 200° C. | good |
| yellowness (DIN 6167/ASTM D 1925-70) | 0.5 |

The impact strength is determined by dropping a die of known weight from a specific height onto the back of the coated surface. The value obtained is the product of the weight of the die in kg and the greatest height in cm at which the coating still remains intact. The flow is assessed visually as fair, good or very good.

This coating system has a greater reactivity and flexibility than a system based on pure diglycidyl terephthalate.

EXAMPLE 7

A powder coating composition comprising 930 g of Crylcoat® 430, 95.5 g of the product of Example 2, 11 g of Acrylron® solid, 3 g of benzoin, 30 g of a catalyst (concentrate of a tetraalkylammonium bromide salt) and 500 g of titanium dioxide is homogenised as described in Example 6. This powder coating composition is sprayed on to an aluminium sheet and stoved for 10 minutes at 200° C. to give a film having the following properties:

| film thickness | 56 μm |
|---|---|
| impact strength | 160 kg · cm |
| Erichsen cupping test (DIN 53156) | 10 mm |
| gloss under an angle of 60° | 90% |
| fklow at 200° C. | good |
| yellowness (DIN 6167/ASTM D 1925-70) | 0 |

This powder coating composition has a greater reactivity and flexibility than a system based on pure diglycidyl terephthalate.

EXAMPLE 8

A powder coating composition comprising 930 g of Crylcoat® 430, 103.5 g of the product of Example 3, 11 g of Acrylron® solid, 3 g of benzoin, 30 g of a catalyst (concentrate of a tetraalkylammonium bromide salt) and 500 g of titanium dioxide is homogenised as described in Example 6. This powder coating composition is sprayed on to an aluminium sheet and stoved for 15 minutes at 200° C. to give a film having the following properties:

| film thickness | 55 μm |
|---|---|
| impact strength | 160 kg · cm |
| Erichsen cupping test (DIN 53156) | 10 mm |
| gloss under an angle of 60° | 94% |
| flow at 200° C. | good |
| yellowness (DIN 6167/ASTM D 1925-70) | 0 |

This powder coating composition has a greater reactivity and flexibility than a system based on pure diglycidyl terephthalate.

EXAMPLE 9

A powder coating composition comprising 930 g of Crylcoat® 430, 120 g of the product of Example 4, 12 g of Acrylron® solid, 3 g of benzoin, 30 g of a catalyst (concentrate of tetraalkylammonium bromide salt) and 525 g of titan dioxide is homogenised as described in Example 6. This powder coating composition is sprayed on to an aluminium sheet and stored for 10 minutes at 200° C. to give a film having the following properties:

| film thickness | 57 μm |
|---|---|
| impact strength | 140 kg · cm |
| Erichsen cupping test (DIN 53156) | 10.4 mm |
| gloss under an angle of 60° | 93% |
| flow at 200° C. | good |
| yellowness (DIN 6167/ASTM D 1925-70) | 0 |

This powder coating composition has a greater reactivity and flexibility than a system based on pure diglycidyl terephthalate.

EXAMPLE 10

9le;1.5q465.6 g (5.03 mol) of epichlorohydrin and 25.6 g of water are heated to a temperature of c. 60° C. Then 30.0 g (0.156 mol) of trimellitic anhydride, 100.4 g of terephthalic acid and 5.1 g of a 50% aqueous solution of tetramethylammonium chloride are added. The temperature is thereafter kept at c. 90° C., and the reaction course is monitored with the aid of a pH electrode. After c. 120 minutes, the pH meter registers a sudden increase to c. 9.4. After removal of the pH electrode, the reaction mixture is cooled to c. 15° C. Then 310.4 g (3.35 mol) of epichlorohydrin and 20.6 g of a 50% aqueous solution of tetramethylammonium chloride are added. Under a vacuum of 120 mbar and at a temperature of 50° C., 154.3 g of an aqueous solution of sodium hydroxide are run in continuously over 300 minutes, while distilling water from the reaction mixture with epichlorohydrin as an azeotropic mixture. The reaction mixture is then washed with 450 ml of water, with 120 ml of an aqueous 5% solution of sodium bisulfate and then with 200 ml of water and concentrated under a water jet vacuum.

Yield: 204.4 g (90% of theory) of a solid product (melting point 99.9° C.; epoxy value 6.86 epoxide equivalents/kg; chlorine content 0.63%).

What is claimed is:

1. A powder coating composition, which contains as curing agent a solid polyglycidyl composition which is substantially free of inert components comprising
   (a) at least one polyglycidyl compound having a molecular weight of less than about 1500 that is solid at ambient temperature; and
   (b) at least about 5% by weight based on the total amount of polyglycidyl compounds in the composition of:
      (i) at least one polyglycidyl compound having a molecular weight of less than about 1500 that is liquid at said ambient temperature; or
      (ii) a mixture of polyglycidyl compounds, each compound having a molecular weight of less than about 1500, which mixture is liquid at said ambient temperature;
   wherein the polyglycidyl component (a) that is solid at ambient temperature is chemically different from the polyglycidyl component (b) that is liquid at said ambient temperature; and
   wherein at least a portion of the polyglycidyl component (a) is present in the composition in the form of one solid mixed phase or a mixture of more than one solid mixed phase, which solid mixed phase or mixture of more than one solid mixed phase contains substantially the total amount of the polyglycidyl component (b) that is present in the composition.

2. A powder coating composition according to claim 1, which is based on polyesters containing free carboxyl groups.

3. A powder coating composition according to claim 1, wherein the solid polyglycidyl compounds are diglycidyl esters which are selected from the group consisting of diglycidyl terephthalate, diglycidyl isophthalate, diglycidyl trans-hexahydrophthalate, diglycidyl oxalate, diglycidyl adipate, diglycidyl sebacate, diglycidyl azelate and diglycidyl succinate.

* * * * *